(12) United States Patent
Allers et al.

(10) Patent No.: US 6,287,273 B1
(45) Date of Patent: Sep. 11, 2001

(54) PERFUSION SYSTEM

(75) Inventors: Mats Allers; Krasnodar Ivancev; Bengt Jeppson, all of Lund (SE)

(73) Assignee: Argmed Kommanditbolag, Bjarred (SE)

( * ) Notice: Subject to any disclaimer, the term of this patent is extended or adjusted under 35 U.S.C. 154(b) by 0 days.

(21) Appl. No.: 09/357,124

(22) Filed: Jul. 20, 1999

(30) Foreign Application Priority Data

Jul. 10, 1999 (SE) .................................................. 9902682

(51) Int. Cl.$^7$ ...................................................... A61M 1/00
(52) U.S. Cl. ................................................. 604/27; 604/96
(58) Field of Search ............................. 604/4.01, 35, 28, 604/43, 27, 96.01, 97.01, 97.03, 98.01, 101.01, 101.02, 101.03, 101.04, 101.05, 102.01–102.03, 171, 192, 194; 606/191–194

(56) References Cited

U.S. PATENT DOCUMENTS

| | | |
|---|---|---|
| 4,192,302 | 3/1980 | Boddie . |
| 4,540,402 | 9/1985 | Aigner . |
| 4,655,746 | 4/1987 | Daniels et al. . |
| 4,714,460 | 12/1987 | Calderon . |
| 4,883,459 | 11/1989 | Calderon . |
| 5,308,320 | 5/1994 | Safar et al. . |
| 5,433,700 | 7/1995 | Peters . |
| 5,458,574 | 10/1995 | Machold et al. . |
| 5,478,309 | 12/1995 | Sweezer et al. . |
| 5,702,368 | 12/1997 | Stevens et al. . |
| 5,746,717 | 5/1998 | Aigner . |
| 5,817,046 | 10/1998 | Glickman . |

FOREIGN PATENT DOCUMENTS

| | | |
|---|---|---|
| 0420488 | 4/1991 | (EP) . |
| 0554082 | 8/1993 | (EP) . |
| 0274411 | 7/1998 | (EP) . |
| 0876805 | 11/1998 | (EP) . |
| 0364799 | 4/1999 | (EP) . |
| WO 8806045 | 8/1988 | (WO) . |
| WO 9524940 | 9/1995 | (WO) . |
| 96 00103 | 1/1996 | (WO) . |
| 96 40350 | 12/1996 | (WO) . |
| 97 17101 | 5/1997 | (WO) . |
| WO 9929363 | 6/1999 | (WO) . |
| 99 33407 | 7/1999 | (WO) . |
| WO 9933407 | 7/1999 | (WO) . |

*Primary Examiner*—Manuel Mendez

(57) ABSTRACT

A perfusion system for non-surgically isolating and perfusing an organ, particularly the liver (101), in a patient, and including; by-pass cathether apparatus having inlet and outlet lumens (111, 112) introducible into the blood vessels of the organ percutaneously and devised so as to by-pass the blood flow past the organ in a by-pass circuit; perfusion catheter apparatus having inlet and outlet lumens (114, 116) introducible into the blood vessels percutaneously and being devised so as to lead the flow of perfusion fluid in a perfusion circuit through the organ; occlusive seals (106, 108) for isolating the organ from the systemic blood flow; pump apparatus including a by-pass pump (261), a perfusion fluid pump (124) and a suction pump (134) for establishing a negative relative pressure at the perfusion outlet from the organ; and control apparatus (128) coupled to the pumps (124, 126, 134) so as to control the operation thereof such that the outflow of fluid from the organ exceeds the inflow of fluid into the organ in the perfusion circuit due to a net volume contribution of blood from the systemic circulation entering the isolated organ.

34 Claims, 3 Drawing Sheets

PERFUSION SYSTEM

TECHNICAL FIELD

The present invention relates to a system and a method for non-surgical perfusion of an organ in a living being, in particular non-surgical perfusion of a liver.

BACKGROUND

Treatment with systemic chemotherapy is one of the presently used possibilities in cancer treatment. However, substances that are effective in this kind of treatment are often harmful to the system of the body as a whole. Particularly, the treatment of cancer of the liver presents a serious clinical problem, and the success rate when treating liver cancer is today very low.

Although primary liver cancer (hepatoma) is rather uncommon in northern Europe and United States, hepatoma is prevalent in other parts of the world, e.g. in Southeast Asia, Japan, the Pacific Islands, Greece, Italy and parts of Africa. Also, many patients with cancer in the gastrointestinal tract develop isolated hepatic metastases, since the liver is the primary target for dissemination. Due to the distribution of the metastases within the liver, only few patients with liver cancer can be cured by resection.

Liver cancer is today mainly treated with systemic chemotherapy. However, no substantial increase in the time of survival of the patients is following this treatment (L. M. De Brauw *"Isolated liver perfusion. An experimental modality in the treatment of hepatic metastases."* Thesis, University of Leiden, Leiden, The Netherlands.). A reason for these discouraging results seems to be the fact that the toxicity of the chemodrugs limits the possible dosage due to the systemic effects. Local administration by infusion in the hepatic artery does not solve this problem, since the chemodrugs are distributed in the system also during this procedure.

STATE OF THE ART

In order to administrate therapeutic drugs locally it has been suggested to perform perfusion of selected organs.

In EP-0 364 799 to BGH Medical Productions, which is hereby incorporated by reference, a process of perfusing a high concentration of an agent through an organ is described. The agent is infused arterially in the organ and on the venous side of the organ the blood is removed from the body using a specially designed double balloon catheter. In this process there is a leakage to the systemic blood flow, since there are numerous blood communicating vessels besides the main artery and the main vein.

A similar catheter is used in the U.S. Pat. No. 5,817,046 to Glickman et al., which is hereby incorporated by reference, showing a system for perfusion of the pelvic cavity. The pelvic cavity is isolated between a double catheter, placed in the iliac vein, and bilateral thigh tourniquets. The thigh tourniquets, which are used to restrict the flow of blood between the legs and the pelvic cavity of the patient, limit the time during which perfusion can be performed.

In U.S. Pat. No. 4,714,460 to Calderon, which is hereby incorporated by reference, feedback methods and systems for retrograde perfusion in the body are described. A double balloon concentric catheter, with an inner infusion lumen and an outer suction lumen, is used for perfusion of the venous side of the vascular network. The therapeutic agent for treatment is infused inside the vein in the opposite direction with respect to the ordinary blood flow, also called retrograde incision. The described method is, thus, designed to operate in back pressure and the perfusion fluid is continuously diluted by arterial blood.

U.S. Pat. No. 4,883,459 to Calderon, which is hereby incorporated by reference, describes a method for perfusion where a carrier medium dye is injected into the tumor. The flow of the dye is monitored to determine an optimal retrograde perfusion path through the tumor.

A balloon catheter with closed tip and device for perfusion with such catheters, are described in U.S. Pat. No. 5,746,717 to Aigner, which is hereby incorporated by reference. The catheter has at least one contrast marking which enables the position of the catheter inside the body to be determined.

The perfusion processes and apparatuses described above all include the return of the blood, which has been contaminated with drugs, to the systemic circulation. This requires treatment to remove the contaminants before this blood can be returned to the body.

An assembly for hepatic isolation and perfusion is described in U.S. Pat. No. 4,192,302 to Boddie, which is hereby incorporated by reference. This assembly allows the blood from the intestines and the lower parts in the patient's body to flow unimpeded through a plurality of shunts. Meanwhile, the blood in the isolated liver is circulated using a heart-lung machine, which allows cancericidal doses of drugs to be delivered to liver cancers essentially without systemic effects. However, the procedure involved is complicated and the large operation, which is needed to place the shunts, only permits perfusion once inter alia due to scars in the tissues and the severe stress on the body of the patient.

Consequently, a drawback with some of the above mentioned, earlier procedures for organ perfusion is that the organ may not be isolated in a perfusion circuit, thus, perfusion fluid may easily leak into the systemic circulation. Another drawback is that blood, which is used to perfuse the organ, may after perfusion contain therapeutic agents, and thus, needs to be purified before it is returned to the body. In the case of a surgical method, as the one described in U.S. Pat. No. 4,192,302, it is a disadvantage that the perfusion can only be performed once on each patient due to the large operation involved. A particular disadvantage with the prior art occurs when there is a considerable fraction of the blood flow that does not enter or leave the organ through the main input and output blood vessels, which for example is the case in the liver, and there is a risk for leakage of perfusion fluid through these minor vessels to the systemic circulation. The venous side of the liver is close the heart, thus leakage of drugs to the system would potentially very fast cause harm.

OBJECT OF THE INVENTION

The object of the present invention, and the problem to be solved, is to provide a system for a minimally invasive perfusion of an organ and a method for minimally invasive perfusion, in other words a system and a method for non-surgically isolating and perfusing an organ. A particular object is to provide such a method and system that allow for a prolonged and increased therapeutic effect. Another object and an aspect of the problem to be solved is to decrease the risk of leakage of therapeutic agents, being locally delivered to an essentially isolated organ in a dosage which is harmful for the body as a whole. A further object and aspect of the problem is to provide a method and a system for easily maintaining and controlling flows and pressures of the blood and perfusion fluid in the organ to be perfused and in the body as a whole.

SUMMARY OF THE INVENTION

The object of the invention is achieved by a system and a method for isolating and perfusing an organ, wherein the main inflow as well as the outflow, vessels of the organs are blocked by means of percutaneously introducible occlusive seals. In addition to the occlusive seals, percutaneously introducible passages or conduits preferably in the form of catheters are placed in the main inflow and outflow vessels in order to establish a shunted blood flow for bypassing the normal blood flow of the organ as well as in order to establish an open or a closed circuit for circulating a perfusion fluid.

The invention is based on the inventor's realization that, for this kind of operation to be efficient in terms of repeatability and of sparing the patient unnecessary stress that diminishes the positive effect of the treatment, the operation has to be carried out non-surgically. This has been made possible by means of percutaneous catheter technology and specifically designed catheters and perfusion equipment in accordance with the invention.

The important advantages of the invention is that the perfusion treatment is invasive to a minimum and therefore repeatable in an unlimited number of treatment occasions. The treatment is also very lenient and would normally take about 2–4 hours in total compared to about 10–12 hours with an invasive, surgical method. Very little stress is therefore imposed on the organism. This entails a substantial saving for the individual patient receiving the treatment as well as for the society bearing the costs of health care and loss of work during treatment.

In a step by step description, the method comprises the steps of isolating and perfusing the organ by:

(a) sealing off the main input and output blood vessels of the organ by means of percutaneously introducible occlusive seals, such that said organ becomes essentially isolated from the systemic blood circulation;

(b) establishing a bypass circuit by means of percutaneously introducible bypass catheter lumens, whereby the systemic blood is bypassed past said organ;

(c) establishing a perfusion circuit by means of percutaneously introducible perfusion catheter lumens, into which perfusion circuit said organ is connected;

(d) circulating a perfusion fluid in said perfusion circulation that the perfusion fluid perfuses the organ.

The method further comprises the step of: establishing a negative pressure at the outlet of the organ into the perfusion circuit, such that the outflow of said organ is slightly higher than the inflow from the perfusion circuit, whereby the perfusion fluid is supplied with a net volume contribution of blood from the systemic circulation entering the essentially isolated organ. In this way, it is assured that a leakage of perfusion fluid, often containing a hazardous chemodrug, to the systemic circulation is avoided.

The system according to the invention comprises a catheter set specifically devised to be percutaneously introducible into the blood vessels close to the organ, a pump apparatus for circulating a perfusion fluid and bypassed blood, and a perfusion control apparatus for controlling the operation of the pump apparatus and other components of the system.

The catheter set comprises:

(1) bypass catheter means being percutaneously introducible into the main inflow and outflow blood vessels of the organ and being devised to lead the systemic blood flow past the organ in a partially extracorporeal bypass circuit;

(2) perfusion catheter means being percutaneously introducible into the main inflow and outflow blood vessels of the organ and being devised to lead the flow of perfusion fluid through the organ in a partially extracorporeal perfusion circuit; and (3) occlusive seals being percutaneously introducible in the main inflow and outflow blood vessels and being devised to seal off the main blood inflow and outflow of said organ such that the occlusive seals separate the bypass circuit from the perfusion circuit;

The pump apparatus for maintaining a flow in said bypass and perfusion circuits, said pump apparatus comprises:

(1) a bypass pump, which is couplable to the extracorporeal parts of the bypass circuit, for pumping the blood in said bypass circuit;

(2) a perfusion pump, which is couplable to the extracorporeal part of the perfusion circuit, for pumping a perfusion fluid in said perfusion circuit; and (3) means for establishing a negative relative pressure at the perfusion circuit outlet at the organ.

The perfusion control apparatus is couplable to the pump apparatus and is devised to control the operation of said pumps such that the outflow of fluid from the organ exceeds the inflow of fluid into the organ in the perfusion circuit due to a net volume contribution of blood from the systemic circulation entering the isolated organ.

Other components and advantages of the invention are described in the detailed description of the invention below.

BRIEF DESCRIPTION OF THE DRAWINGS

The invention is described in conjunction with the accompanying drawings in which.

DETAILED DESCRIPTION OF EMBODIMENT OF THE INVENTION

The invention is a method and a system for performing perfusion of an essentially isolated organ in order to perfuse said organ with a perfusion fluid, which may contain a therapeutic agent. The perfusion can either be performed in antegrade or in retrograde. Antegrade perfusion means that the flow of the perfusion fluid in the perfused organ is of the same direction as the normal systemic blood flow and retrograde means that the perfusion flows are redirected compared to the normal blood flow in the perfused organ. According to some embodiments of the invention, retrograde perfusion provides certain advantages that will be explained below.

Figure 1:
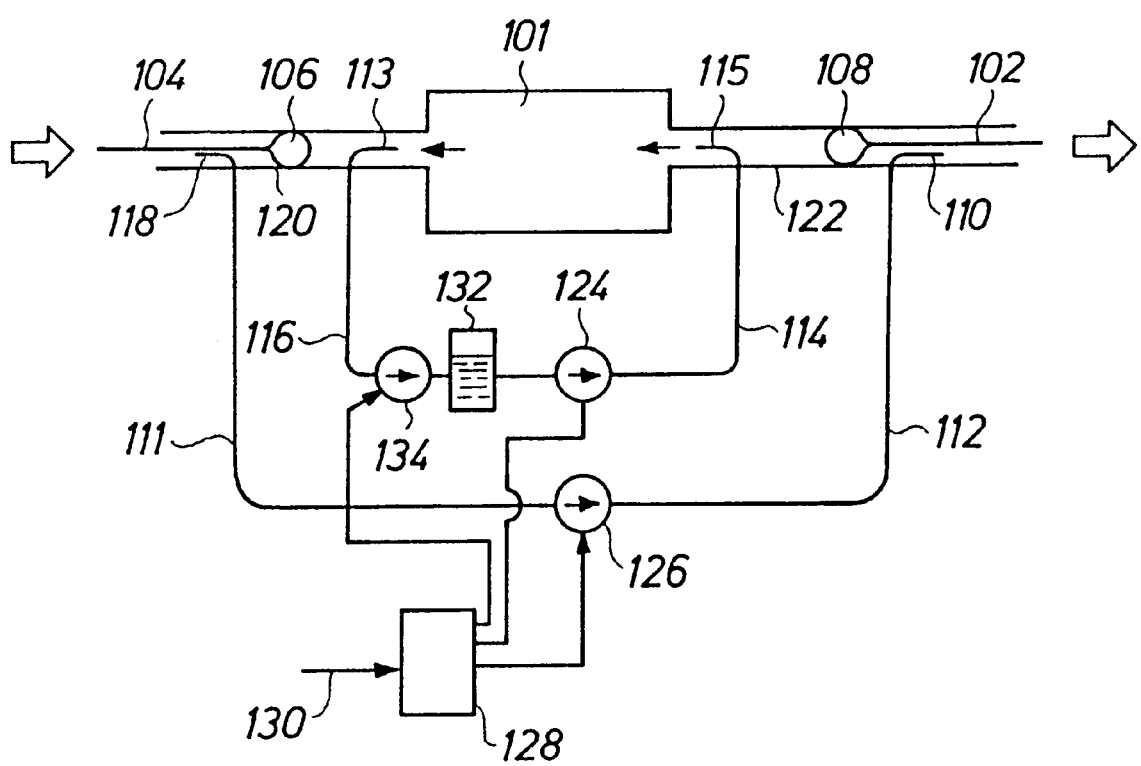
FIG. 1 shows a general block diagram of the system according to the invention.

FIG. 1 shows an organ 101 having a main blood input vessel 120 and a main blood output vessel 122. The normal direction of the blood flow is illustrated by thick arrows and perfusion fluid direction by thin arrows. The input vessel 120 and the output vessel 122 are sealed off by means of percutaneously introducible occlusive seals 106 and 108 such that the organ is essentially isolated from the systemic blood flow. Bypass catheter means, comprising bypass inlet 111 and outlet 112 conduits or lumens, are percutaneously introduced into the blood vessels to establish a bypass path.

The conduits are placed such that the distal opening 118 of the bypass inlet lumen 111 is placed upstream the occlusive seal 106, and such that the distal opening 110 of the bypass inlet lumen is placed downstream the second occlusive seal 108. The proximal ends of the bypass conduits are connected to a bypass pump 126 devised for pumping blood in tie bypass path formed by the bypass lumens.

Perfusion catheter means, comprising perfusion inlet 114 and outlet 115 conduits or lumens, are percutaneously introduced into the blood vessels to establish a perfusion circuit. The perfusion conduits are placed such that the distal opening 113 of the perfusion outlet lumen 116 is placed between the output of the organ and the occlusive seal 106, and the distal opening of the perfusion inlet lumen 114 is placed between the input of the organ and the occlusive seal 108. The proximal end of the inlet perfusion lumen 114 is coupled via a perfusion fluid pump 124, e.g. a roller pump, coupled to a pension fluid reservoir 132 containing a perfusion fluid. The perfusion fluid pump is devised to pump perfusion fluid from the reservoir at a controllable pressure or flow rate. The proximal end of the outlet perfusion lumen 116 is coupled to means 134 for establishing a negative, relative pressure, e.g. a suction pump in the form of a roller pump or other kinds of pumps. By maintaining a negative relative pressure on the perfusion circuit outlet side of the essentially isolated organ the flows in the conduits of the perfusion circuit is controlled such that the outflow of the organ is equal or, preferably, slightly higher than the inflow. Accordingly, the perfusion fluid is supplied with a net volume contribution of blood from the systemic circulation entering the essentially isolated organ through minor blood vessels. This technique will minimize the risks of leakage of perfusion fluid from the perfusion circuit to the systemic circulation. In addition, if the blood flow in minor veins contribute substantially to the outflow of the organ, the risks of leakage is further decreased in the embodiment of the invention where the perfusion is performed in retrograde. This is due to that in this case the flow in the minor veins is then redirected, while in the minor arteries there is a natural back pressure.

A control apparatus 128 coupled to the pumping means and provided with a control command input 130 is also shown in FIG. 1. The control apparatus is devised to control the operation of the pumps such that the outflow of fluid from the organ exceeds the inflow of fluid into the organ in the perfusion circuit due to a net volume contribution of blood from the systemic circulation entering the isolated organ. When there is a net volume contribution from the systemic blood, it assured that a minimum of perfusion fluid leaks out of the organ. The required net contribution is different for different patients, but as an exemplifying rule the content of the reservoir should rise slowly by about 5–10 ml/minute in an amount of perfusion fluid which is nominally about 430–500 ml.

Embodiments of the perfusion system further includes different parameter sensors for sensing e.g. flow rate, pressure, temperature and the like.

In practice, preferably using percutane and interventional radiological techniques a set of catheters is, according to one preferred embodiment of the method and the system of the present invention, placed as described above when the patient is under anesthetic. In the case of antegrade perfusion die system comprises catheters which are placed as in the following description of the method. A first catheter, having a lumen and an occlusive seal, is thus placed with a distal end on the venous side of the organ in as close proximity to the organ as possible. Said first catheter is the outlet from the organ to the perfusion circuit. A second catheter, having a lumen and an occlusive seal, is placed with a distal end on the arterial side of the organ, said catheter being the inlet to the organ in the perfusion circuit. A third catheter, having a lumen, is placed with a distal end on the side where blood normally enters said organ, wirihich side usually is arterial, and upstream the occlusive seal of said second catheter. A fourth catheter, having a lumen, is placed wiith a distal end downstream the occlusive seal of said first catheter in the main output blood vessel of the organ. The proximal ends of said first and second catheter are connected to form an, at least partially, extracorporeal perfusion circuit into which the organ to be perfused is connected. The proximal ends of catheter three and four are connected to form an, at least partially, extracorporeal bypass circuit through which the blood in the systemic circulation is bypassed said essentially isolated organ. The catheters axe extracorporeally connected through tubing, which in one embodiment is isolated in order to preserve the appropriate temperature. Both circuits are connected to pumps for pumping. When all catheters are in place, the systemic blood circulation through said organ is blocked and the circulation is started in the bypass circuit and perfusion circuit, respectively. In accordance with a preferred embodiments of the invention the perfusion fluid in the perfusion circuits is connected to a supply for therapeutic agent.

Leakage from the perfusion circuit is, in one embodiment of the invention, controlled by adding a substance to the perfusion fluid, which substance can be detected in the systemic blood circulation. For example could a carrier medium dye, which is directly visible by imaging, be used as an initial control of the perfusion circuit. Another substance, for example a radio marked substance is added together with the therapeutic agent and intermittently analyzed blood samples from peripheral circulation or continuously controlled by an extra-corporeal meter capable of measuring radioactivity a blood vessel.

The invention can be used for repeated local treatments of various organs, i.e. organs which mainly have well define input and out blood vessels such as kidney, liver, pancreas, bladder and pelvis. The invention is particularly advantageous with retrograde perfusion of an essentially isolated organ, which type of perfusion is preferred in cases when there is a considerable fraction of the blood flow which does not enter or leave the organ through the main input and output blood vessels, for example in case of the liver.

Each treatment can proceed a period of time during which the body can manage without having the systemic blood circulation in contact with the perfused organ. After treatment the perfusion circuit is normally filled up with uncontaminated fluid, for example blood which may have been drawn from the patient at an earlier time or taken from another blood supply, in order to secure that drugs used for treatment do not spread systemically.

Figure 2:
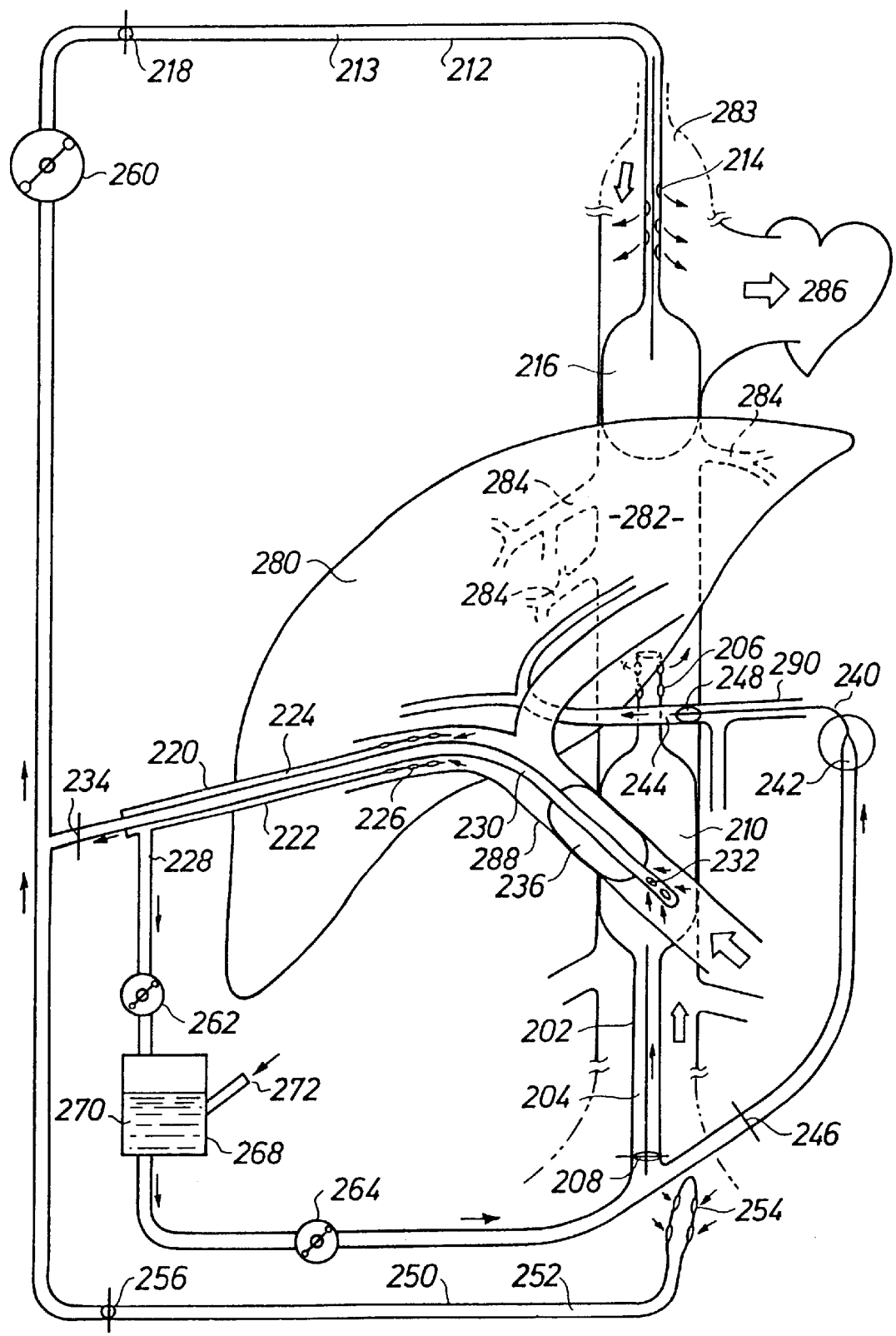
FIG. 2 shows a schematic drawing of a liver connected to the system for retrograde perfusion according to one embodiment of the invention.

An embodiment of the invention applied on a liver in a human patient is schematically shown in FIG. 2. The perfusion is in this example carried out in retrograde on an isolated liver 280. The flow direction in catheters is illustrated by thin arrows and the perfusion lumen 204 and an occlusive seal 210, is placed in the inferior vena cava 282 of the patient such that the seal is placed closed to upstream, below in FIG. 2, the hepatic veins 284 and the distal end opening 205 of the lumen 204 is positioned downstream said occlusive seal 210 preferably at level with the hepatic veins. It is important that the occlusive seal 210 is situated below the liver 280, since at the stretch of vena cava inferior 282 which is embedded in the liver there are numerous minor veins entering vena cava inferior from the liver. Furthermore, the seal must be placed and devised such that the veins from the kidneys, entering in vena cava inferior, are not blocked, The first catheter 202 is for example introduced via vena femoralis and is preferably devised to be placed in French, the occlusive seal of said first catheter being devised to be capable of efficiently sealing off vena cava inferior upstream the hepatic veins.

A second catheter 212, having a bypass lumen 213 and an occlusive seal 216, is placed in the inferior vena cava 282 of the patient such that the seal 216 is placed between the heart 285 and the hepatic veins 284 and the distal end opening 214 of the bypass lumen 213 ends on the proximal side of the occlusive seal 216. The second catheter 212 is introduced via vena cava superior 283 and is devised to be placed in French, the occlusive seal of said first catheter being devised to be capable of efficiently sealing off vena cava inferior upstream the hepatic veins.

A second catheter 212, having a bypass lumen 213 and an occlusive seal 216, is placed in the inferior vena cava 282 of the patient such that the seal 216 is placed between the heart 286 and the hepatic veins 284 and the distal end opening 214 of the bypass lumen 213 ends on the proximal side of the occlusive seal 216. The second catheter inferior 282 by means of an introducer having a maximum outer diameter of 14 French, the occlusive seal of said second catheter being capable to efficiently seal off vena cava inferior between the hepatic veins 284 and the heart 286 without blocking any of the hepatic veins.

A third catheter 220 is placed in vena porta 228. The third catheter is devised to be place in vena porta percutaneously and trans-hepatically by means of an introducer with a maximum outer diameter of 12 French. The third catheter is provided with an introducer 222, having an introducer lumen 224 with distal 226 and proximal 228 end openings and being devised to operate as a perfusion lumen, a bypass lumen 230 with distal 232 and proximal 234 end openings and an occlusive seal 236. The third catheter is devised such that the occlusive seal is positioned between said distal end opening of the bypass lumen and said distal end opening of the introducer lumen during operation of the system. Vena porta 288 branches into several veins before it enters the liver and the seal 236 of said third catheter 220 must be placed upstream these branches. The vena porta is difficult to enter due to its position between the liver and the intestinal parts. According to the invention vena porta is therefore entered through the liver, which due to its structure is relatively undamaged.

A fourth catheter 240 is placed in the hepatic artery 290. The fourth catheter is provided with a perfusion inlet lumen 242 with distal 244 and proximal 246 end openings and an occlusive seal 248, said distal end opening being positioned distally of the occlusive seal. The fourth catheter 240 is devised to be placed in the hepatic artery 290 by means of an introducer with a maximum outer diameter of 5 French, the occlusive seal of said fourth catheter being capable to efficiently seal off the hepatic artery.

A fifth catheter 250 is placed in vena cava inferior 282 upstream the occlusive seal 210 of the first catheter 202. The fifth catheter is provided with a bypass lumen 252 with distal 254 and proximal 256 end openings, and is devised to be placed in vena cava inferior by means of an introducer having a maximum outer diameter of 14 French.

A partially extracorporeal bypass circuit is formed by connecting the proximal end opening 256 of the lumen of said fifth and the proximal end opening 234 of the bypass lumen of said third catheter to a bypass pump 260. The bypass pump 260, e.g. a roller pump, is further coupled to the proximal end opening 218 of the bypass lumen of said second catheter. In the bypass circuit the venous blood from the lower parts of the body is taken out through the fifth catheter and is, together with the venous blood from the intestines taken out through the lumen of the third catheter, reentered into the systemic blood circulation above the liver 280 through the second catheter 212.

A partially extracorporeal perfusion circuit is formed by connecting the proximal end opening 228 of the introducer lumen of said introducer 222 of said third catheter with a perfusion fluid reservoir 268 via means for establishing a negative relative pressure, e.g. a pump perhaps in the form of a roller pump. The proximal end opening 208 of the lumen of the first catheter 202 and the proximal end opening 246 of the lumen of the fourth catheter are connected to the reservoir 268 via a pump 264, e.g a roller pump. The perfusion fluid is pumped from the reservoir into the hepatic veins 284 and the hepatic artery 290, and to the reservoir from vena porta. The portal vein (vena porta) is advantageous to use for establishing a negative relative pressure at the perfusion outlet of the liver, since it is surrounded and strengthened by a relatively rigid structure which prevents the portal vein from collapsing. In embodiments of the invention when this feature does not occur in the vessels entering or leaving the organ to be perfused, it is conceivable to provide, at the perfusion outlet opening of a catheter, a structure devised to prevent the vessel from collapsing, for example in the form of a stent.

Figure 3:
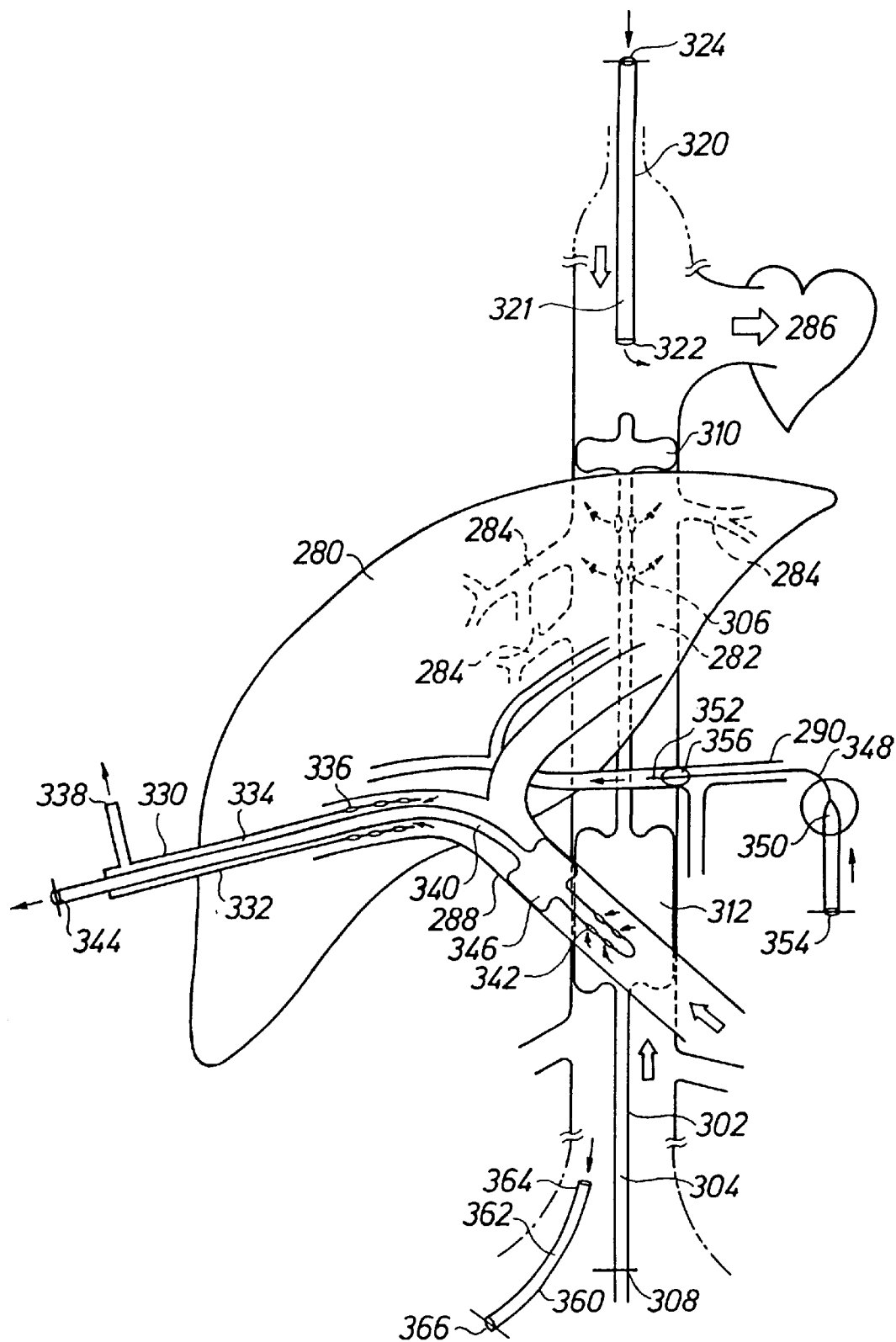
FIG. 3 shows a schematic drawing of a liver connected to the system for retrograde perfusion according to another embodiment of the invention.

Another embodiment of the invention applied on a liver in a human patient is schematically shown in FIG. 3. The perfusion is also in tis example carried out in retrograde on an isolated liver 280. The flow direction in catheters is illustrated by thin arrows and the normal direction of the systemic blood flow by thick arrows.

A first catheter 302 is placed in vena cava inferior, said first catheter having a perfusion lumen 304 with distal 306 and proximal 308 end openings and a first occlusive seal 310 being positioned distally of said distal end opening and a second occlusive seal 312 being positioned proximally of said distal end opening 306. The first catheter 302 is devised to be placed in vena cava inferior 282 by means of an introducer having a maximum outer diameter of 14 French, the first occlusive seal of said first catheter being capable to efficiently seal off vena cava inferior between the heart 286 and the hepatic veins 284, and the second occlusive seal of said first catheter being capable to efficiently seal off vena cava inferior 282 below the hepatic veins 284.

A second catheter 320 is placed in vena cava inferior, said second catheter having a bypass lumen 321 with distal 322 and proximal 324 end openings. The second catheter 320 is devised to be placed in vena cava inferior by means of an introducer having a maximum outer diameter of 14 French.

A third catheter 330 is placed in vena porta 288, the third catheter being provided with an introducer 332, having an introducer lumen 334 with distal 336 and proximal 338 end openings and being devised to operate as a perfusion lumen, said catheter having a bypass lumen 340 with distal 342 and proximal 344 end openings and an occlusive seal 346, said third catheter being devised such that the occlusive seal is positioned between said distal end opening of tie bypass lumen and said distal end opening of the introducer lumen during operation of the system. The third catheter 330 is devised to be placed percutaneously and transhepatically in vena porta by means of an introducer with a maximum outer diameter of 12 French, the occlusive seal of said third catheter being devised to be capable of efficiently sealing off vena porta.

A fourth catheter 348 is placed in the hepatic artery 290, said fourth catheter having a perfusion inlet lumen 350 with distal 352 and proximal 354 end openings and an occlusive seal 356, said distal end opening being positioned distally of the occlusive seal. The fourth catheter 348 is devised to be placed in the hepatic artery by means of an introducer with a maximum outer diameter of 5 French, the occlusive seal of said fourth catheter being capable to efficiently seal off the hepatic artery.

A fifth catheter 360 is placed is placed in the inferior vena cava upstream or below the occlusive seal 312 of the first catheter 302. The fifth catheter is merely provided with a bypass lumen 362 with distal 364 and proximal 366 end openings.

The embodiment of FIG. 3 is coupled in an analougue with the embodiment of FIG. 2.

A second catheter 212, having a bypass lumen 213 and an occlusive seal 216, is placed in the inferior vena cava 282 of the patient such that the seal 216 is placed between the heart 286 and the hepatic veins 284 and the distal end opening 214 of the bypass lumen 213 ends on the proximal side of the occlusive seal 216. The second catheter 212 is introduced via vena cava superior 283 and is devised to be placed in vena cava inferior 282 by means of an introducer having a maximum outer diameter of 14 French, the occlusive seal of said second catheter being capable to efficiently seal off vena cava inferior between the hepatic veins 284 aid the heart 286 without blocking any of the hepatic veins.

A third catheter 220 is placed in vena porta 288. The third catheter is devised to be placed in vena porta percutaneously and trans-hepatically by means of an introducer with a maximum outer diameter of 12 French. The third catheter is provided with an introducer 222, having an introducer lumen 224 with distal 226 and proximal 228 end openings and being devised to operate as a perfusion lumen, a bypass lumen 230 with distal 232 and proximal 234 end openings and an occlusive seal 236. The third catheter is devised such that the occlusive seal is positioned between said distal end opening of the bypass lumen and said distal end opening of the introducer lumen during operation of the system. Vena porta 288 branches into several veins before it enters the liver and the seal 236 of said third catheter 220 must be placed upstream these branches. The vena porta is difficult to enter due to its position between the liver and the intestinal parts. According to the invention vena porta is therefore entered through the liver, which due to its structure is relatively undamaged.

A fourth catheter 240 is placed in the hepatic artery 290. The fourth catheter is provided with a perfusion inlet lumen 242 with distal 244 and proximal 246 end openings and an occlusive seal 248, said distal end opening being positioned distally of the occlusive seal. The fourth catheter 240 is devised to be placed in the hepatic artery 290 by means of an introducer with a maximum outer diameter of 5 French, the occlusive seal of said fourth catheter being capable to efficiently seal off the hepatic artery.

A fifth catheter 250 is placed in vena cava inferior 282 upstream the occlusive seal 210 of the first catheter 202. The fifth catheter is provided with a bypass lumen 252 with distal 254 and proximal 256 end openings, and is devised to be placed in vena cava inferior by means of an introducer having a maximum outer diameter of 14 French.

The extra-corporeal parts of the bypass and perfusion circuits consist mainly of tubing which is connected to the proximal ends of the catheters through per se known connections. In this embodiment these connections are e.g. luer lock connections, but other types of connections such as screw connections are conceivable.

By sealing off the flow of blood as described above the liver is essentially isolated from the systemic circulation. Although, there is still a number of minor arteries and veins which still connect the organ to the rest of the body 200. Before starting the circulation in the bypass and the perfusion circuits, the circuits are filled with fluid in order to ensure that air does not enter the body through the circuits. Circulating the blood past the liver in the bypass circuit is achieved by pumping. The pressure of the venous blood in the lower parts of the body and in vena porta is not high enough to press the blood all the way to the outlet of the perfusion circuit. It is, however, critical that the normal blood pressure upstream the seal 236,346 of the third catheter in vena porta is maintained and without the bypass circuit there pressure would build up in vena porta. Such a pressure increase could cause severe problems due to open arteries in the flow to the lower part of the body. With a closed venous return path to the upper part of the body, there would be a blood congestion with a following fall of blood pressure in the upper part of the body. It is also necessary to compensate for the blood volume which is cut off from the systemic circulation in the perfusion circuit when the bypass circulation is started and therefore blood is added to the patient.

As described above, a perfusion fluid reservoir is connected to the perfusion lumens. The perfusion fluid is withdrawn from the perfused organ by establishing a negative relative pressure at the perfusion outlet from the organ. Such a negative relative pressure is in a simple embodiment achieved by arranging a relative difference in height between the reservoir and the perfused organ, e.g. by means of a vertically movable mounting of the reservoir. In other embodiments a more active suction is for example, achieved by pumping or by lowering the pressure above the fluid in the perfusion fluid reservoir.

Therapeutic agents to be used for treatment of the perfusion liver is entered into the perfusion circulation through the perfusion fluid reservoir. When the treatment is finished the perfusion circuit is filled with uncontaminated fluid and the organ is filled with this clean blood before the occlusive seals are unsealed and the circulation is turned off.

In one embodiment heating equipment, devised to heat the fluid in the perfusion circuit, and an oxygenator devised to oxygenate the fluid in perfusion circuit is also included. It has been found that the efficiency of therapeutic agents often can be enhanced by selecting an appropriate temperature and degree of oxygenization.

Embodiments of the system of the present invention includes means for exchanging the fluid in the perfusion circuit after finished treatment, such means are for example a T-valve in the perfusion circuit tubing, which valve is connected to a supply of uncontaminated fluid.

The circulation in the perfusion and the bypass circuits is in preferred embodiments maintained and controlled by means of a perfusion apparatus comprising two pumps, a perfusion fluid reservoir and a control apparatus. A heart-lung, machine may, when operated by a very skilled person however also, be used as perfusion apparatus The system further comprises a substance to be added to the perfusion fluid for enabling control of potential leakage to the systemic circulation and/or a substance to be added to the fresh blood or the perfusion fluid for enabling control of the exchange of perfusion fluid with fresh blood.

The invention has been described by means of exemplifying embodiments, bit is defined by the scope of the accompanying claims.

What is claimed is:

1. A perfusion system for non-surgically isolating and perfusing an organ in the body of a living being with a perfusion fluid, comprising:

a set of catheters including, (1) bypass catheter means having inlet and outlet conduits and being percutaneously introducible into the main inflow and outflow, blood vessels of the organ and being devised to lead the systemic blood flow past the organ in a partially extracorporeal bypass circuit;

(2) perfusion catheter means having inlet and outlet conduits being percutaneously introducible into the main inflow and outflow blood vessels of the organ and being devised to lead the flow of perfusion fluid through the organ in a partially extra-corporeal perfusion circuit; and (3) occlusive seals being percutaneously introducible between distal end openings of the bypass conduits and the perfusion conduits in the main inflow and outflow blood vessels and being devised to seal off the main blood inflow and outflow of said organ such that the occlusive seals separate the bypass circuit from the perfusion circuit.

2. The perfusion system of claim 1, wherein the catheter means of said set of catheters includes:

(a) a first catheter, having a perfusion lumen with distal and proximal end openings and an occlusive seal, said distal end opening being positioned distally of the occlusive seal;

(b) a second catheter, having a bypass lumen with distal and proximal end openings and an occlusive seal, said distal end opening being positioned proximally of the occlusive seal;

(c) a third catheter with an introducer, having an introducer lumen with distal and proximal end openings and being devised to operate as a perfusion lumen, said catheter having a bypass lumen with distal and proximal end openings and an occlusive seal, said third catheter being devised such that the occlusive seal is positioned between said distal end opening of the bypass lumen and said distal end opening of the introducer lumen during operation of the system;

(d) a fourth catheter, having a perfusion inlet lumen with distal and proximal end openings and an occlusive seal, said distal end opening being positioned distally of the occlusive seal; and (e) a fifth catheter, having a bypass lumen with distal and proximal end openings.

3. The perfusion system of claim 2, wherein the catheter means of said set of catheters is devised for isolating and perfusing the liver of a living being and:

(a) the first catheter is devised to be placed in vena cava inferior by means of an introducer having a maximum outer diameter of 14 French, the occlusive seal of said first catheter being capable to efficiently seal off vena cava inferior upstream the hepatic veins;

(b) the second catheter is devised to be placed in vena cava inferior by means of an introducer having a maximum outer diameter of 14 French, the occlusive seal of said second catheter being capable to efficiently seal off vena cava inferior between the hepatic veins and the heart;

(c) the third catheter is devised to be placed percutaneously and trans hepatically in vena porta by means of an introducer with a maximum outer diameter of 12 French, the occlusive seal of said third catheter being capable to efficiently seal off vena porta; and (d) the fourth catheter is devised to be placed in the hepatic artery by means of an introducer with a maximum outer diameter of 5 French, the occlusive seal of said fourth catheter being capable to efficiently seal off the hepatic artery.

4. The perfusion system of claim 1, wherein the catheter means of said set of catheters includes;

(a) a first catheter, having a perfusion lumen with distal and proximal end openings and a first occlusive seal being positioned distally of said distal end opening and a second occlusive seal being positioned proximally of said distal end opening;

(b) a second catheter, having a bypass lumen with distal and proximal end openings;

(c) a third catheter with an introducer, having an introducer lumen with distal and proximal end openings and being devised to operate as a perfusion lumen, said catheter having a bypass lumen with distal and proximal end openings and an occlusive seal, said third catheter being devised such that the occlusive seal is positioned between said distal end opening of the bypass lumen and said distal end opening of the introducer lumen during operation of the system;

(d) a fourth catheter, having a perfusion inlet lumen with distal and proximal end openings and an occlusive seal, said distal end opening being positioned distally of the occlusive seal; and (e) a fifth catheter, having a bypass lumen with distal and proximal end openings.

5. The perfusion system of claim 4, wherein the catheter means of said set of catheters is devised for isolating and perfusing the liver of a living being and:

(a) the first catheter is devised to be placed in vena cava inferior by means of an introducer having a maximum outer diameter of 14 French, the first occlusive seal of said first catheter being capable to efficiently seal off vena cava inferior between the heart and the hepatic veins, and the second occlusive seal of said first catheter being capable to efficiently seal off vena cava inferior below the hepatic veins;

(b) the second catheter is devised to be placed in vena cava inferior by means of an introducer having a maximum outer diameter of 14 French;

(c) the third catheter is devised to be placed percutaneously and trans hepatically in vena porta by means of an introducer with a maximum outer diameter of 12 French, the occlusive seal of said third catheter being capable to efficiently seal off vena porta; and (d) the fourth catheter is devised to be placed in the hepatic artery by means of an introducer with a maximum outer diameter of 5 French, the occlusive seal of said fourth catheter being capable to efficiently seat off the hepatic artery.

6. The perfusion system of claim 1 further comprising:

(4) a pump apparatus for maintaining a flow in said bypass and perfusion circuits, said pump apparatus having:

(a) a bypass pump, which is couplable to the extracorporeal parts of the bypass circuit, for pumping the blood in said bypass circuit, for pumping the blood in said bypass circuit;

(b) a perfusion pump, which is couplable to the extra-corporeal part of the perfusion circuit, for pumping a perfusion fluid in said perfusion circuit; and (c) means for establishing a negative relative pressure at the distal end of the perfusion outlet conduit; and (5) a perfusion control apparatus, which is couplable to said pump apparatus and devised to control the operation of said pump apparatus such that the outflow of fluid from the organ exceeds the inflow of fluid into the organ in the perfusion circuit due to a net volume contribution of blood from the systemic circulation entering the isolated organ.

7. The system of claim 6, further comprising a perfusion reservoir devised to be connectable to the extra-corporeal part of the perfusion circuit such that a perfusion fluid in the perfusion circuit passes through the reservoir.

8. The system of claim 7, wherein the perfusion reservoir is devised to enable vertical movement of the reservoir for establishing mid controlling a negative relative pressure at a distal end opening of a perfusion outlet conduit.

9. The system of claim 7, further comprising a vacuum source being connectable to the perfusion reservoir and devised for establishing and controlling a negative relative pressure at a distal end opening of a perfusion outlet conduit.

10. The system of claim 7, further comprising a suction pump being connectable to the extra-corporeal part of the perfusion circuit and devised for establishing a negative relative pressure at a distal end opening of a perfusion outlet conduit.

11. The system of claim 6, further comprising:
a heating equipment devised to heat a perfusion fluid in the perfusion circuit; and
an oxygenator devised to oxygenate a perfusion fluid in the perfusion circuit.

12. The system of claim 1, further comprising means for exchanging a first perfusion fluid with a second perfusion fluid during operation of the system.

13. The system of claim 6, further comprising a leakage indicating substance devised to be added to a perfusion fluid for enabling detection of leakage to the systemic blood circulation during operation of the system.

14. The system of claim 6, further comprising a fluid exchange substance devised to be added to a perfusion fluid for enabling monitoring and control of the exchange of a first perfusion fluid with a second perfusion fluid during operation of the system.

15. The system of claim 6, wherein the bypass inlet and outlet conduits and the perfusion inlet and outlet conduits are lumens of catheters.

16. The system of claim 6, wherein the bypass inlet and outlet conduits and the perfusion inlet and outlet conduits are lumens of catheter introducers.

17. The system of claim 6, wherein the occlusive seals are occlusion balloons of balloon catheters.

18. The system of claim 6, wherein the organ of the living being, which is connected to the perfusion circuit, is a liver.

19. The perfusion system of claim 1 further comprising,
(4) a pump apparatus having:
(a) a first pump which is couplable to an extracorporeal conduit of a bypass circuit though which the systemic blood circulation is bypassed an essentially isolated organ;
(b) a second pump which is couplable to an extracorporeal conduit of a perfusion circuit, through which circuit a perfusion fluid perfuses the essentially isolated organ;
(c) means for establishing negative relative pressure at the distal end of the perfusion outlet conduit;
(d) a perfusion reservoir, which is connectable into the perfusion circuit between the outlet from the essentially isolated organ and the second pump, and to which a drug supply is connectable; and
whereby an essentially isolated organ can be connected to a perfusion circuit with circulating perfusion fluid, and the natural bloodstream is bypassed past said organ through a bypass circuit, said circuits being connected to the perfusion apparatus.

20. The perfusion system of claim 1 further comprising:
(4) a control apparatus for controlling the perfusion of an organ in the body of a living being with a perfusion fluid, including:
(a) pressure control device, to control blood pressures and pressure of a perfusion fluid in a perfusion circuit;
(b) a temperature control device, to control temperatures in the body of a living being in the perfusion fluid; and
(c) a flow rate control device to, control flow rates in the perfusion circuit and a bypass circuit;
the control apparatus being couplable to said perfusion pump apparatus.

21. The perfusion system of claim 20, wherein the control apparatus further comprises a level control device, to control the level in a perfusion reservoir of a perfusion apparatus.

22. The perfusion system of claim 20 wherein the control apparatus further comprises a device for controlling an automated valve between a perfusion reservoir and a reservoir for fresh blood being couplable to an extra-corporeal perfusion circuit and being devised to switch between the perfusion reservoir and the reservoir in case of a detected leakage from the perfusion circuit to the systemic blood circulation.

23. A method for non-surgically essentially isolating and perfusing an organ in a body of a living being, comprising the steps of:
(a) sealing off the main input and output blood vessels of said organ by means of percutaneously introducing seals in said main blood vessels, such that said organ becomes essentially isolated from the systemic blood circulation;
(b) establishing a bypass circuit by means of percutaneously introducing bypass conduits having distal and proximal ends with openings, placing the distal ends in the main input and output blood vessels of said organ and connecting the proximal ends by an extracorporeal conduit, through which bypass circuit the systemic blood is bypassed past said organ;
(c) establishing a perfusion circuit by means of percutaneously introducing perfusion conduits having distal and proximal ends with openings, placing the distal ends in the main input and output blood vessels of said organ and connecting tie proximal ends by an extra-corporeal conduit, into which perfusion circuit the organ is connected;
(d) circulating a perfusion fluid in said perfusion circuit so that the perfusion fluid perfuses the organ.

24. The method of claim 23, further comprising the step of:
establishing a negative pressure at the distal end of a perfusion conduit said perfusion conduit being the outlet from the organ into the perfusion circuit, such that the outflow of said organ is slightly higher than the inflow from the perfusion circuit,
whereby the perfusion fluid is supplied with a net volume contribution of blood from the systemic circulation entering the essentially isolated organ.

25. The method of claim 23, wherein the step of sealing off the main input and output blood vessels comprises:
(a) percutaneously placing occlusive seals in main output blood vessels of said organ for enabling the main blood flow out from said organ to be sealed off;
(b) percutaneously placing occlusive seals in main input blood vessels for enabling the main blood flow in to said organ to be sealed off; and
(c) sealing off the blood inflow and outflow of said organ, by means of said occlusive seals, such that the organ is essentially isolated from the systemic blood circulation.

26. The method of claim 23, wherein the step of establishing a bypass circuit comprises:
(a) percutaneously introducing bypass inlet and bypass outlet conduits having a distal and a proximal ends with openings, such that the distal end openings of said conduits are positioned in main blood vessels on the outside, compared to the organ, of the occlusive seals for sealing off the main organ output and input blood vessels; and
(b) connecting the proximal end openings of said bypass inlet and outlet conduits through conduits to an partially extracorporeal bypass circuit.

27. The method of claim 23, wherein the step of establishing a perfusion circuit comprises:
(a) percutaneously placing perfusion inlet and perfusion outlet conduits having a distal and a proximal ends with openings, such that the distal end openings of said conduits are positioned in main blood vessels on the organ side of the occlusive seals for sealing off the main organ output and input blood vessels; and
(b) connecting the proximal end openings of said perfusion inlet and outlet conduits to an extracorporeal perfusion circuit.

28. The method of claim 23, further comprising the step of:
circulating the systemic blood past said organ in the bypass circuit.

29. The method of claim 23, further comprising the step of:
adding drugs to the perfusion fluid in the perfusion circuit so that it perfuses through the organ.

30. The method of claim 23, wherein the placing of occlusive seals, perfusion conduits and bypass conduits is performed by the placing of percutaneously introducible catheters.

31. The method of claim 23, wherein the perfused organ is a liver in the body of a living being.

32. The method of claim 23, wherein the pension is performed in retrograde such that a perfusion inlet lumen is placed such that the distal end opening is positioned in a blood vessel with the normal blood flow out from the organ and a perfusion outlet lumen is placed such that its distal end opening is positioned in a blood vessel with the normal blood flow in to the organ.

33. A method for non-surgically isolating and perfusing a liver in the body of a living being without using surgery, comprising the steps of:
(a) placing, percutaneously, a first catheter, having a lumen with distal and proximal end openings and an occlusive seal, in the inferior vena cava of the patient such that the seal is positioned upstream the liver and he distal end openings of the lumen is positioned downstream said occlusive seal;
(b) placing, percutaneously, a second catheter, having a lumen with distal and proximal end openings and an occlusive seal, in the inferior vena cava of the patient such that the seal is positioned downstream the vena hepatica and the distal end openings of the lumen is positioned downstream of said occlusive seal;
(c) placing, percutaneously and trans-hepatically, a third catheter by mean of an introducer, having an introducer lumen with distal and proximal end openings, the catheter having a lumen with distal and proximal end openings and an occlusive seal, in the vena porta of the patient such that the distal end openings of the lumen is positioned upstream the distal end openings of the introducer lumen and the seal is positioned between the distal end openings of said introducer lumen and said lumen;
(d) placing a fourth catheter, having a lumen with distal and proximal end openings and an occlusive seal, in the hepatic artery of the patient such that the distal end openings of the lumen is positioned downstream said occlusive seal;
(e) placing a fifth catheter, having a lumen with distal and proximal end openings, in the inferior vena cava, such that the distal end opening of said lumen ends upstream of the occlusive seal of said first catheter;
(f) connecting the proximal ends openings of the lumens of the third and the fifth catheters with the proximal end openings of the lumen of the second catheter, such that a partially extracorporeal bypass circuit is formed;
(g) connecting the proximal end opening of the introducer lumen of said introducer for the third catheter with the proximal end openings of the lumens of the first and the fourth catheters, such that a partially extracorporeal perfusion circuit is formed;
(h) sealing off the flow of blood past the occlusive seal in the inferior vena cava with said seal of said first catheter;
(i) sealing off the flow of blood past the occlusive seal in the inferior vena cava with said seal of said second catheter;
(j) sealing off the flow of blood past the occlusive seal in the vena porta with the said seal of said third catheter;
(k) sealing off the flow of blood past the seal in the arteria hepatica with said seal of said fourth catheter;
(l) circulating the blood past said organ in said bypass circuit;
(m) establishing a negative relative pressure at the distal end of the perfusion outlet lumen; and
(n) circulating a perfusion fluid in said perfusion circuit so that the perfusion fluid perfuses the organ, such that the outflow of said organ is equal to or slightly higher than the inflow and the perfusion fluid is supplied with a net volume contribution of blood from the systemic circulation entering the essentially isolated organ.

34. A method for non-surgically isolating and perfusing a liver in the body of a living, being without using surgery, comprising the steps of:
(a) placing, percutaneously, a first catheter, having a lumen with distal and proximal end openings and a first and a second occlusive seal, in he inferior vena cava of the patient such that the first occlusive seal is positioned between the heart and the hepatic veins, the second occlusive seal is positioned downstream the hepatic veins, and the distal end openings of the lumen is positioned between said first occlusive seal and second occlusive seal;
(b) placing, percutaneously, a second catheter, having a lumen with distal and proximal end openings, in the inferior vena cava of the patient such that the distal end opening is positioned between the heart and said first occlusive seal of the first catheter;

(c) placing, percutaneously and trans-hepatically, a third catheter by means of an introducer, having an introducer lumen with distal and proximal end openings, the catheter having a lumen with distal and proximal end openings and an occlusive seal, in the vena porta of the patient such that die distal end openings of he lumen is positioned upstream the distal end openings of the introducer lumen and the seal is positioned between the distal end openings of said introducer lumen and said lumen;

(d) placing a fourth catheter, having a lumen with distal and proximal end openings and an occlusive seal, in the hepatic artery of the patient such that the distal end openings of the lumen is positioned downstream said occlusive seal;

(e) placing a fifth catheter, having a lumen with distal and proximal end openings, in the inferior vena cava, such that the distal end opening of said lumen ends upstream of said second occlusive seal of said first catheter;

(f) connecting the proximal ends openings of the lumens of the third and the fifth catheters with the proximal end openings of the lumen of the second catheter, such that a partially extracorporeal bypass circuit is formed;

(g) connecting the proximal end opening of the introducer lumen of said introducer for the third catheter with the proximal end openings of the lumens of the first and the fourth catheters, such that a partially extracorporeal perfusion circuit is formed;

(h) sealing off the flow of blood past the occlusive seal in the inferior vena cava with said seal of said first catheter;

(i) sealing off the flow of blood past the occlusive seal in the inferior vena cava with said seal of said second catheter;

(j) sealing off the flow of blood past the occlusive seal in the vena porta with the said seal of said third catheter;

(k) sealing off the flow of blood past the seal in the arteria hepatica with said seal of said fourth catheter, (l) circulating the blood past said organ in said bypass circuit;

(m) establishing a negative relative pressure at the distal end of the perfusion outlet lumen; and (n) circulating a perfusion fluid in said perfusion circuit so that the perfusion fluid perfuses the organ such that the outflow of said organ is equal to or slightly higher than the inflow and the perfusion fluid is supplied with a net volume contribution of blood from the systemic circulation entering the essentially isolated organ.

* * * * *